United States Patent
Gusenbauer et al.

(10) Patent No.: US 10,259,464 B2
(45) Date of Patent: Apr. 16, 2019

(54) CONTROL FOR AN ELECTRONIC MULTI-FUNCTION APPARATUS

(71) Applicant: Bayerische Motoren Werke Aktiengesellschaft, Munich (DE)

(72) Inventors: Dominik Gusenbauer, Seattle, WA (US); Olga Karsunke, Munich (DE); Anastasia Petrou, Munich (DE); Christian Spies, Munich (DE); Markus Strassberger, Wartenberg (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 0 days.

(21) Appl. No.: 15/724,316

(22) Filed: Oct. 4, 2017

(65) Prior Publication Data
US 2018/0022359 A1 Jan. 25, 2018

Related U.S. Application Data

(63) Continuation of application No. PCT/EP2016/056771, filed on Mar. 29, 2016.

(30) Foreign Application Priority Data

Apr. 9, 2015 (DE) .......... 10 2015 206 334
Apr. 9, 2015 (DE) .......... 10 2015 206 336

(51) Int. Cl.
*A61B 5/00* (2006.01)
*A61B 5/18* (2006.01)
(Continued)

(52) U.S. Cl.
CPC .......... *B60W 40/08* (2013.01); *A61B 5/18* (2013.01); *A61B 5/681* (2013.01); *B60W 50/08* (2013.01);
(Continued)

(58) Field of Classification Search
CPC .................. G08B 21/06; A61B 5/18
(Continued)

(56) References Cited

U.S. PATENT DOCUMENTS

2004/0070509 A1* 4/2004 Grace .......... A61B 5/1103
340/575
2004/0214615 A1 10/2004 Entenmann et al.
(Continued)

FOREIGN PATENT DOCUMENTS

DE  10 2008 038 816 A1  2/2010
DE  10 2011 084 887 A1  4/2013
(Continued)

OTHER PUBLICATIONS

German-language Search Report issued in counterpart German Application No. 10 2015 206 334.8 dated Nov. 15, 2016 with partial English translation (13 pages).
(Continued)

*Primary Examiner* — Fabricio R Murillo Garcia
(74) *Attorney, Agent, or Firm* — Crowell & Moring LLP

(57) ABSTRACT

A method and system for controlling at least one predefined function of an electronic multi-function apparatus usable during travel by a vehicle driver is provided. The electronic multi-function apparatus is connected to a control unit of the vehicle by a communication link. Data of the vehicle driver and/or data on the journey is acquired, and on the basis of the acquired data at least one characteristic value which is characteristic of the degree of loading of the vehicle driver by his current vehicle control process is formed. The at least one predefined function of the electronic multi-function apparatus is controlled based on the at least one characteristic value in such a way that a degree of loading of the vehicle driver when using the function is matched to the
(Continued)

degree of loading of the vehicle driver corresponding to the current vehicle control process.

25 Claims, 3 Drawing Sheets

(51) Int. Cl.
| | | |
|---|---|---|
| *G06K 9/00* | (2006.01) | |
| *B60W 40/08* | (2012.01) | |
| *B60W 50/08* | (2012.01) | |
| *B60W 50/14* | (2012.01) | |
| *B60W 50/16* | (2012.01) | |

(52) U.S. Cl.
CPC ............ *B60W 50/14* (2013.01); *B60W 50/16* (2013.01); *G06K 9/00845* (2013.01); *A61B 5/6893* (2013.01); *A61B 2503/10* (2013.01); *B60W 2040/0872* (2013.01); *B60W 2050/146* (2013.01)

(58) Field of Classification Search
USPC ......................................................... 340/439
See application file for complete search history.

(56) References Cited

U.S. PATENT DOCUMENTS

| | | |
|---|---|---|
| 2008/0125937 A1 | 5/2008 | Decke et al. |
| 2012/0244849 A1 | 9/2012 | Thomson |
| 2013/0038437 A1 | 2/2013 | Talati et al. |
| 2013/0044215 A1 | 2/2013 | Rothkopf et al. |
| 2013/0288606 A1 | 10/2013 | Kirsch |
| 2014/0342717 A1 | 11/2014 | Chen et al. |
| 2014/0375477 A1 | 12/2014 | Jain et al. |
| 2015/0216466 A1* | 8/2015 | Kronberg ................. A61B 5/18 702/19 |
| 2015/0242190 A1 | 8/2015 | Roelle et al. |
| 2015/0251663 A1* | 9/2015 | Yang ...................... G08B 21/06 701/1 |
| 2016/0052524 A1* | 2/2016 | Kim ...................... B60W 40/09 340/576 |
| 2016/0274922 A1 | 9/2016 | Steidle et al. |

FOREIGN PATENT DOCUMENTS

| | | |
|---|---|---|
| DE | 10 2012 213 965 A1 | 2/2014 |
| DE | 10 2012 220 787 A1 | 6/2014 |
| DE | 10 2013 221 867 A1 | 4/2015 |
| DE | 10 2013 224 279 A1 | 5/2015 |
| DE | 10 2014 214 078 A1 | 1/2016 |
| EP | 1 467 543 A2 | 10/2004 |
| WO | WO 2006/119788 A1 | 11/2006 |

OTHER PUBLICATIONS

German-language Search Report issued in counterpart German Application No. 10 2015 206 336.4 dated Mar. 21, 2016 with partial English translation (12 pages).
International Search Report (PCT/ISA/210) issued in PCT Application No. PCT/EP2016/056771 dated Jun. 28, 2016 with English translation (5 pages).
German-language Written Opinion (PCT/ISA/237) issued in PCT Application No. PCT/EP2016/056771 dated Jun. 28, 2016 (6 pages).

* cited by examiner
CONTROL FOR AN ELECTRONIC MULTI-FUNCTION APPARATUS

CROSS REFERENCE TO RELATED APPLICATIONS

This application is a continuation of PCT International Application No. PCT/EP2016/056771, filed Mar. 29, 2016, which claims priority under 35 U.S.C. § 119 from German Patent Applications Nos. 10 2015 206 334.8 and 10 2015 206 336.4, both filed Apr. 9, 2015, the entire disclosures of which are herein expressly incorporated by reference.

BACKGROUND AND SUMMARY OF THE INVENTION

The invention relates to a method, a system and a computer program product for controlling an electronic multi-function device. The invention relates in particular to a method, a system and a computer program product for controlling a function of an electronic multi-function device used in a vehicle, and to a corresponding vehicle. The invention relates in particular to the corresponding controller in conjunction with the use of a portable electronic multi-function device in a vehicle. The invention further relates in particular to a controller for a multi-function watch. The multi-function watch can, for example, be worn by a vehicle driver on the arm while driving in a vehicle.

In vehicles, in particular motor vehicles such as automobiles, trucks, buses and motorcycles, nowadays more and more electronic multi-function devices are installed and/or carried and used by vehicle drivers during the journey. On electronic multi-function devices a plurality of applications and/or functions is usually available. An application can provide at least one function. The application can be in particular a computer program which is loaded into a data memory of the multi-function device and runs on a microprocessor of the multi-function device and thereby provides the at least one function.

Corresponding electronic multi-function devices may be permanently fitted to the vehicle, for example as a vehicle entertainment system, or integrated into a vehicle control unit. They can also be not permanently connected to the vehicle in the form of mobile portable electronic multi-function devices, and instead be carried on the user's person for traveling and/or carried in the vehicle temporarily. Such mobile portable multi-function devices can be carried in the vehicle either undetached or temporarily fastened to and/or easily detachable from the vehicle. They can be connected to control units and/or power supply units of the vehicle using communications technologies, for example by cables and/or wireless means. For example, they can be connected via a vehicle socket to an on-board electrical network of the vehicle to provide an energy supply. They typically include at least one input interface and/or output interface, which can be used as a user interface (human machine interface, HMI).

An electronic multi-function device can be, for example, a CE terminal. It can be an audio and/or video device, such as an MP3 player, a DVD playback device, a video camera, a radio and/or television set. It can also be a game console, a computer, in particular a laptop or a tablet PC, a mobile phone or an electronic multi-function watch.

Electronic multi-function watches, which are also designated by the term smart watches, are electronic multi-function devices, which comprise at least one timepiece function and can be worn on the body by means of a wrist strap like a standard wristwatch. They also comprise at least one radio interface for setting up a wireless communication link to other electronic devices.

By means of the communication link, a smart watch can be networked with other devices, such as a computer and/or a computer network, in particular with the internet, for data exchange. The radio interface used can be designed according to any desired radio standard, for example the Bluetooth standard, a mobile wireless standard in accordance with the Global System for Mobile Communications (GSM), G2, G3, G4 and/or G5, the near field standard (NFC) and/or a standard for Wireless Local Area Network (WLAN) in accordance with the IEEE 802.11 family, etc.

In addition, similarly to smartphones, tablet PCs and other computers, smart watches usually offer the facility of optionally installing user software programs, so-called apps. The user can therefore equip his smart watch in a very individual way according to his personal needs.

In principle, a smart watch can have all the features of a smartphone mobile wireless device. A smart watch can also comprise sensors for collecting a wide variety of physical, in particular physiological and/or medical parameters, for example a temperature sensor, a moisture sensor, a pulse sensor, a blood pressure sensor and/or a position sensor, e.g. for recording the geographical position based on the global positioning system, GPS. A smart watch, which is worn directly on the body via an armband, offers in particular due to the bodily contact the opportunity for body function data, such as pulse and blood pressure, to be recorded directly using the sensors of the smart watch. The values detected can also be output directly on the smart watch by means of an output unit such as a display, so that they can be easily recorded by the user. A smart watch may also comprise one or more inertial sensors such as, e.g., an acceleration sensor, a gyroscope and/or a magnetometer, which can be used in particular for capturing motion data, for motion detection and/or motion classification, e.g. for so-called fitness tracking. Smart watches also often have a tactile interface. Such an interface is suitable for outputting a tactile signal or a tactile feedback, e.g. for a vibration alarm.

An electronic multi-function device can also comprise an interface for a wireless and/or for a wired communication with another electronic device. In particular, access to a communication network can be available in the multi-function device, for example to a mobile wireless network in accordance with a mobile radio standard. An electronic multi-function device can also comprise at least one other interface for setting up a data connection to other devices, for example a Universal Serial Bus (USB) interface for a wired connection, a Wireless Local Area Network (WLAN) interface for a wireless radio connection to a computer network and/or a Near Field Communication (NFC) interface and/or a Bluetooth interface for a wireless connection to another electronic device.

In an electronic multi-function device at least one sensor for a physical, a physiological and/or a medical parameter can also be provided. An electronic multi-function watch designed as a so-called smart watch comprises at least one timepiece function and can be worn on the body by means of a wrist strap like a normal wristwatch.

Electronic multi-function devices also offer the facility of computer programs for additional functions and applications. An application can be provided in particular by means of a so-called app. These apps can be loaded into the multi-function device by the user of the multi-function device as a computer program (software), in particular from an external data source such as a so-called App Store, in particular via the internet, and installed there. For example, for the iOS operating system used in electronic multi-function devices from Apple Inc., an App Store under the name of iTunes is known, and for the Android operating system from Google Inc. used in electronic multi-function devices from various manufacturers, an App Store under the name Google Play is known. In an App Store a selection can be made from a plurality of applications, for example from action games to online newspapers.

As mobile electronic multi-function devices, in particular multi-function mobile wireless devices, also called smartphones, are often used. These are devices, in particular mobile telephones, with which a mobile wireless connection for a voice and/or data connection can be set up in accordance with at least one mobile radio communication standard and with which in addition, multiple other functions can be used. Known mobile radio standards are, e.g., standards of the Global System for Mobile Communications (GSM), such as G2, G3, G4 and G5. In addition to a mobile wireless connection, smartphones often also offer the facility for other communication links, e.g. for connection by Bluetooth, NFC, USB, WLAN etc., which have already been mentioned above.

Electronic multi-function devices, and in particular smartphones, are often used when traveling in vehicles. Especially popular, for example, is the use of a corresponding multi-function device on which a navigation system is installed as an app. A desired destination can be entered in the navigation system, for example, before the start of the journey and the driver of the vehicle is guided along a calculated route to his destination by means of a graphical representation on a display of the multi-function device and/or by an acoustic output of navigation commands via a loudspeaker of the multi-function device. Other apps, for example for playing audio files such as music or audiobooks, can also be used effectively in a vehicle.

BMW AG has released an app under the name BMW Connected, which allows convenient switching between different vehicle compatible apps while driving. The switching can be performed using an input and/or output system in the vehicle, such as a vehicle display, an audio system and/or a rotary/pressure actuator (known under the name of BMW iDrive). Other apps installed on a multi-function device, such as a smartphone, can also be conveniently used, for example for social networks such as Facebook and Twitter, calendar functions etc., comfortably and ergonomically by means of the vehicle-internal input/output system without the driver of the vehicle having to handle the multi-function device.

DE 10 2012 220 787 A1 has described a system in which in a vehicle one or more vehicle parameters and/or personal parameters of at least one person using the vehicle are provided, and depending on the parameters a state variable is determined, on the basis of which a graphic object is selected, which is displayed in a graphical output device of the vehicle.

In the German Patent Application No. DE 10 2013 224 279.4 submitted by the applicant and not previously published, a system was disclosed for providing a user of a motor vehicle with an assistance function of an assistant located outside of the vehicle over a communication link, which is available via the assistant and selected by the user. The particular helper can be a human or else a non-human agent. The assistance function can be provided in particular on the basis of a signal which is generated when a problem situation of the vehicle or the user is detected. The detection means used here can be a device either fitted in the vehicle or carried in it, which records information on a current status of the motor vehicle and/or the user. In particular, the use of one or more sensors arranged in the vehicle, such as a camera, can be provided.

In the Patent Application No. DE 10 2013 221 867.2 submitted by the applicant and not previously published, it was disclosed that a control device in a motor vehicle is connected to a driving situation sensor, which generates a signal describing the driving situation. The control device is designed such that a response time for an input device of the motor vehicle is controlled depending on the driving situation. The response time, with which a further input is possible following input to the input device, is extended if a predetermined driving situation is reached.

US 2013/0044215 A1 discloses a flexible electronic display surface that can be worn as an armband, which can be used for a smart watch, for example.

In US 2013/0288606 A1, a system has been described with which different devices can be linked to control units on a vehicle via a radio interface.

The contents of the above publications and patent applications are hereby incorporated into this description by reference.

When an electronic multi-function device and the apps installed on it are used by a vehicle driver while driving, it is very important that the driver of the vehicle is distracted as little as possible from his task of driving by its use.

The object of the invention is to support the safe control of a vehicle by a vehicle driver who uses at least one function of an electronic multi-function device while driving.

According to a first aspect of the invention, to control at least one predefined function, which can be used by a vehicle driver in a vehicle while driving, of an electronic multi-function device, which is connected to a control unit of the vehicle by a communication link, the following steps are provided:

collecting data of the vehicle driver and/or data from the journey, forming, on the basis of the acquired data, at least one characteristic value which is characteristic of the degree of stress of the vehicle driver due to his current vehicle control, controlling the at least one predefined function of the electronic multi-function device using the at least one characteristic value, in such a way that a degree of stress of the vehicle driver when using the function is matched to the degree of stress of the vehicle driver corresponding to his current vehicle control.

The at least one predefined function of the electronic multi-function device by which the characteristic value can be controlled in particular by a control unit of the electronic multi-function device. The control unit may in particular comprise a computer program, which is loaded in a memory of the electronic multi-function device and is executed in a micro-processor of the electronic multi-function device, so that at least a part of the steps according to the invention is effected, and in particular the step of controlling the at least one predefined function of the electronic multi-function device using the characteristic value. The computer program can in particular be provided in a central server as a so-called app for downloading into the electronic multi-function device. In particular, the data for the journey can be at least partially recorded by a control unit, using a sensor of the vehicle. The control unit of the vehicle can also comprise a computer program and corresponding means for executing it, such as a memory and microprocessor.

The electronic multi-function device can be permanently integrated in the vehicle or be mobile and portable, and be carried along in the vehicle when driving.

At least a part of the data from the vehicle driver and/or the journey can be recorded in the electronic multi-function device, and in particular by at least one sensor provided therein or connected thereto, and/or a corresponding control device. The data acquired therewith can in particular be transferred to the control device of the vehicle and/or combined with data that were recorded by at least one unit of the vehicle. From the data recorded in either way, the characteristic value and/or a preparatory characteristic value for forming the characteristic value in the electronic multi-function device, can be formed in a control device or data processing device of the motor vehicle and/or in a vehicle-external data processing device, such as a so-called backend computer. A backend computer, sometimes also called a backend server, is a computer that can exchange data with control devices from a plurality of vehicles, and/or by using a communication network such as the internet, can be connected to a control device of a vehicle for communication purposes. It is also possible to exchange data between a plurality of networked computers, to a provide distributed data storage on the networked computers and/or a distributed processing of data on the networked computers in a so-called Cloud computer network. The Cloud network can also comprise control units from a plurality of vehicles.

The predefined function can in particular be deactivated by the characteristic value. The function can also be controlled with regard to function parameters. For example, an audio/video function can be restricted to the audio portion. The at least one characteristic value can be a loading factor for the vehicle driver. In particular, it can represent the current physical, mental and/or emotional stress or strain on the vehicle driver in his current driving situation.

The at least one characteristic value can also represent the current performance of the vehicle driver and therefore constitute a performance figure. The performance figure can then represent in particular the ability of the vehicle driver to complete both his current driving task and/or one expected in a future time interval, in particular within a predefined time limit of, for example, 15 minutes, and at least one more task with a respectively specified physical, mental and/or emotional degree of difficulty with a specified confidence level. The characteristic value can also provide a level of attentiveness of the vehicle driver. Values representing the attentiveness can be recorded, for example, using one or more sensors, such as a sensor that detects the frequency of the driver's eye blinking and/or a sensor that detects jerky movements of the steering wheel on the vehicle and can be used to form the characteristic value. To detect an attention-related value, a test for the vehicle driver can also be carried out, for example a reaction test, in which a reaction time is detected. The test can be carried out while driving or in a driving break, for example, using voice-guided and/or graphically output questions.

The first aspect of the invention is based on the recognition that, for a meaningful and safe use of an electronic multi-function device, and in particular application programs installed thereon, while driving a vehicle it is advantageous to know the current level of stress on the vehicle driver as a result of driving the vehicle. The invention is based on the further recognition that it is advantageous to control the use of the in particular mobile and portable electronic multi-function device or application programs in a targeted way depending on the stress of the vehicle driver. It has also been identified that by controlling, and in particular deactivating, a function of the electronic multi-function device or the application program in a contextual and stress-dependent manner, any distraction of the vehicle driver caused by the function is reduced and, in particular, can be prevented. This enables the safety level when driving the vehicle to be increased. The invention can be advantageously applied in particular to such application programs and/or functions that are consciously and/or unconsciously perceptible to the vehicle driver and/or that cause an interaction with the vehicle driver, for example in such a way that their execution requires at least one input by the vehicle driver on a user interface.

In the context of the invention, a so-called fidelity of the electronic multi-function device or the application program can be adapted according to the situation. This involves adapting a level of interactivity and/or multi-mediality that can be perceived by the vehicle driver. A high fidelity occurs, for example, with a loud sound of an audio playback or with a large number of moving images of a video playback, or with a plurality of objects being reproduced, in particular displayed on a display unit, which are changing rapidly. A low fidelity, on the other hand, occurs for example in the case of a text block output on a display unit, which changes only relatively slowly, for example only once within a few minutes. To control the fidelity, one possibility is to allow a new interaction step only every n seconds (where n is a predefined whole number depending on the control objective), to stop displaying moving images, etc. As part of the control it is also possible to control the number of applications available to the vehicle driver and/or to control functions of the multi-function device. This can also involve using the complexity or the degree of loading of the user or vehicle driver due to the application/function as control parameters.

The invention can in particular be used to achieve the advantage that the interaction logic or user control of the electronic multi-function device or application program in which the function to be controlled and in particular disabled is provided is adapted to the available cognitive, emotional and/or physical potential of the vehicle driver in the respective driving situation.

With the invention, an adaptive Human Machine Interface (HMI) can also be created with regard to the particular parameters recorded, by means of which the degree of interface-related distraction of the vehicle driver can be kept relatively low.

In accordance with an advantageous embodiment of the invention it can be provided that the data of the journey and/or from the vehicle driver are collected and/or exchanged by means of at least one sensor and/or at least one control unit of the vehicle and/or by means of an interface. The data can be exchanged in particular by means of a radio interface of the vehicle which is designed to communicate with a vehicle-independent, in particular vehicle-external electronic device, for example with a backend computer.

In accordance with a further advantageous embodiment of the invention, a control unit of the vehicle can provide a driving situation signal. The driving situation signal can be formed on the basis of the characteristic value. It can also be generated depending on a respective vehicle characteristic and/or a personal characteristic value for the vehicle driver. The respective vehicle characteristic is representative, for example, of an operating variable of the vehicle, such as speed, longitudinal acceleration, lateral acceleration, interior temperature, etc. The personal characteristic value is representative, for example, of physiological values of the individual, for a degree of attention of the person etc. Appropriate signals or data can also be received by the vehicle from other vehicles.

Other options for forming, providing and using a driving situation signal which is descriptive of a driving situation, in particular a signal that characterizes a problem situation, are cited for example in the previously mentioned patent applications No. DE 10 2012 220 787.2 and DE 10 2013 224 279.4, which here again are incorporated into this description by reference. The respective driving situation signal or the respective characteristic value can in particular also be transmitted to other vehicles or users outside the vehicle. This means they can be informed about the current driving condition of the vehicle and/or the current condition of the vehicle driver.

The respective driving situation signal or the characteristic value can be preferably transmitted over at least one communications interface, in particular via a radio interface, to the electronic multi-function device. The transmission can take place in particular at the request of the multi-function mobile wireless device and/or in particular in real time.

In accordance with a further advantageous embodiment of the invention, the driving situation signal can contain information about control and/or display options of one or a plurality of control units of the vehicle and/or their cognitive, emotional and/or physical relevance, in other words about a level of the respective stress which the vehicle driver experiences due to the operating or displaying. The driving situation signal can provide relevant information for the current time and/or for a specified period of time. With this embodiment, negative interactions between the electronic multi-function device or the respective options and/or the application programs and units provided in the vehicle, so-called on-board systems of the vehicle, can be avoided.

In accordance with a further advantageous embodiment of the invention, the driving situation signal may comprise an information item about at least one application that can be used in the vehicle. Such an application can be, for example, an app, a driving option, a driver assistance function, a multimedia application, a mobile wireless application, etc. The information can be assigned, for example, to an application currently being used and/or expected to be used or usable in a future predefined time period or from a future time period, e.g. a travel option such as a sport setting of the drive engine and/or the chassis of the vehicle. An app can comprise one or more functions. It can in particular comprise one or more functions that are visible to the user and/or require a user interaction (foreground functions) and include one or more functions that are not visible to the user and/or do not require user interaction (background functions). With the invention, in particular at least one foreground function can be advantageously controlled.

The driving situation signal can in particular contain an information item relating to at least one application or function that either can and/or cannot be used while driving. The information can be provided in particular in the form of a list and/or contain corresponding attributes for usability. For example, applications can be application programs (apps), driving options such as a sport setting for the drive engine and/or the chassis of the vehicle, driver assistance functions, multimedia applications and/or mobile wireless applications.

In the context of another advantageous embodiment, the display, activation, deactivation and/or the usage of a particular function or application of the electronic multi-function device are stored in a memory using appropriate usage data. This advantageously enables logging of the usage, on the basis of which the nature of the usage of the electronic multi-function device and/or the respective application or function, in particular its activation and/or deactivation, can be demonstrated at a later time. In the course of the data storage a signature can also be generated and assigned to the stored data.

In a further advantageous embodiment of the invention a minimum characteristic value can be assigned to a function in the electronic multi-function device or to an application, which identifies a minimum level of attentiveness for a person using the function and the use of the function is prevented if the characteristic value formed from the collected data of the vehicle driver and/or the journey is outside a predefined range relative to the minimum characteristic value, in particular below it.

The data of the vehicle driver can preferably be collected using at least one of the following units:

a sensor of the vehicle, in particular a camera, a microphone, a brightness sensor, a pressure sensor, a temperature sensor, a driving-dynamics sensor which detects, for example, the velocity, acceleration or braking force, a control unit of the vehicle, a radio link of the vehicle, in particular one by which a connection can be set up to the mobile telephone and/or to a vehicle-external computer, a sensor of the electronic multi-function device, a control unit of the electronic multi-function device, the internet, a vehicle-external computer, in particular a database and/or a backend computer. The database used can contain personal data of the vehicle driver, such as medical data, physiological data, etc.

At least a part of the data of the vehicle driver for forming the characteristic value can be preferably collected by the vehicle driver being set at least one specified task during the journey and the solution to the task arrived at by the vehicle driver being evaluated.

A system according to the invention for controlling at least one predefined function, which can be used by a vehicle driver in a vehicle while driving, of an electronic multi-function device, which is connected to a control unit of the vehicle by a communication link, includes:

a detection unit, set up to collect data on the vehicle driver and/or data on the journey, a data-processing unit, which on the basis of the collected data forms at least one characteristic value, which is characteristic of the level of stress on the vehicle driver due to his current vehicle control, a control element, which controls at least one predefined function of the electronic multi-function device by means of the at least one characteristic value, in such a way that a degree of stress of the vehicle driver when using the function is matched to the degree of stress of the vehicle driver corresponding to the current vehicle control process.

The detection unit can include at least one sensor, which is permanently fixed in the vehicle and in particular is connected to the control unit of the vehicle for data communication purposes. The at least one sensor and/or an additional sensor can be provided in the electronic multi-function device.

The control unit can in particular comprise the data processing unit and/or the control element. The multi-function device can in particular comprise the data processing unit and/or the control element.

The communication link may be a fully or partially wired connection or a fully or partially wireless connection. It may in particular comprise a radio link, such as a Bluetooth or WLAN connection. It can also include, e.g., a USB connection. It can also comprise a vehicle bus, such as a Controller Area Network (CAN) bus, a Media Oriented Systems Transport (MOST) bus, a Flexray Bus and/or an Ethernet connection. It can also comprise an internet connection.

The electronic multi-function device can be permanently installed in the vehicle. In particular, it can be a device which comprises a user interface (HMI). It can also be a multimedia device, in particular an entertainment system. It can be a central information input and/or output device, a so-called head unit of a vehicle.

The electronic multi-function device can comprise a microprocessor and an electronic memory, into which an application computer program that is executed on the microprocessor can be loaded. The electronic multi-function device can thus be regarded as a computer. In the context of the invention a corresponding computer program product can be specified, which when loaded and executed on a computer effects a method sequence with method steps which are described in this document. The computer program product can in particular wholly or partially comprise the data processing unit and/or the control element.

In the context of the invention it can in particular be provided that an application computer program, in particular an app, is loaded into a multi-function device permanently installed in the vehicle subsequently to the production process of the vehicle by a vehicle user, in particular by the vehicle driver, and/or used. A function provided by such an application computer program can be advantageously controlled with the invention.

The electronic multi-function device can be in particular a mobile portable device. In particular, it can be a multi-function mobile wireless device (smartphone).

According to a particular aspect of the invention the electronic multi-function device can be in particular a multi-function watch. The invention can in particular be used to support the safe driving of a vehicle by a driver of the vehicle who is wearing an electronic multi-function watch on his arm while driving.

According to a second aspect of the invention, which can be provided independently or in combination with the features described in this document in relation to the first aspect of the invention, a method is provided in which an electronic multi-function watch worn on the arm by a vehicle driver while driving in a vehicle is controlled. The multi-function watch has at least one sensor and one radio interface. The method comprises the following steps:

collecting physiological data of the vehicle driver and/or data from the journey, in accordance with the data collected, switching off at least one predefined function of the multi-function watch by means of a control unit of the multi-function watch.

The physiological data of the vehicle driver can comprise, e.g., his bodily function data such as body temperature, pulse or heart rate, blood pressure, sweat secretion, eye redness and/or pupil size. The data on the journey can include, e.g., the traffic situation in the area of the current vehicle location, data on the driving situation such as speed, longitudinal and/or lateral acceleration, weather situation, external temperature, internal temperature and/or the vehicle status. The control unit can be provided either in the multi-function watch or outside of the multi-function watch, in which case a communication connection, in particular using the radio interface, is preferably provided between the multi-function watch and the external control unit for exchanging sensor data and/or control data. In particular, it can be provided that data collected in the vehicle is sent by a control unit of the vehicle to the multi-function watch via the vehicle radio interface. The specific physiological data acquired on the driver and/or data on the journey are preferably processed using predefined rules for generating an idle signal, which is used to control the switching off of the respective function of the multi-function watch. In an advantageous embodiment of the invention, at least part of the physiological data of the vehicle driver is collected by at least one sensor of the multi-function watch. This is possible in a particularly advantageously way directly on the arm of the driver, by the multi-function watch being in contact with the arm.

The second aspect of the invention is based on the recognition that the use, and in particular the operation, of multi-function devices in a vehicle by the vehicle driver represents a considerable potential distraction, which puts the safe driving of the vehicle at risk. In particular, it was recognized that the use of a multi-function watch has an increased potential for distraction if the driver of the vehicle wears it on his arm or wrist, because if the driver of the vehicle wishes, for example, to read information displayed by the multi-function watch or to manually make an entry on the multi-function watch, then he must both move his arm into a specific appropriate position as well as divert his gaze there. Therefore, during the journey there exists a danger that the vehicle driver becomes inattentive and also the danger that, in the event of a driving maneuver being necessary, the driver does not move his arm or hand into a suitable position on the steering wheel fast enough. This can lead to a dangerous driving situation.

With the special aspect of the invention, in particular at least one function of the multi-function watch is controlled. This means that a greater level of safety in road traffic can be advantageously achieved by one or more functions of the multi-function watch being deactivated, in particular when a further increased potential hazard obtains due to the driver of the vehicle being affected by a health-related condition, e.g. a high temperature or a raised pulse rate. Even if a particular potential hazard is present due to vehicle-related, traffic-induced or weather-related circumstances, a higher level of safety can be achieved in road transport. The fact that the driver of the vehicle knows from experience that the particular function of the multi-function watch is automatically disabled in such special situations, he is in particular less tempted to use this function while driving. Thus, a safety-compromising use of the multi-function watch can be effectively prevented. For example, it is particularly effective if all output functions, in particular all the graphical output functions, are disabled, e.g. by switching off the entire display of the multi-function watch. It is also possible advantageously to deactivate all output functions except for the output of a predefined number of information items, for example only to display information such as the time of day.

With the particular aspect of the invention and in particular with a corresponding system, a notification feature can also be disabled. For example, incoming notifications, in particular all automatically incoming notifications to the multi-function watch such as emails, SMS messages, voice messages and in particular, so-called push notifications from other applications or services on the multi-function watch can be suppressed while driving. This can be used in particular to prevent the message from being displayed on a display device of the multi-function watch and/or a signal such as an audible tone or a tactile signal being output in the form of a vibration as soon as the message is received by the multi-function watch. The suppressed incoming notifications can be moved, e.g. into at least one predefined folder of a file system of the multi-function watch and/or marked as suppressed notifications. This means it is possible both to prevent a distraction of the vehicle driver by such notifications while driving, and also allow the notifications received while driving but which were suppressed to be easily identified and easily read after the journey.

The second aspect of the invention enables different input data for controlling the respective function deactivation to be merged, in a particularly advantageous way. With this aspect, it is also possible to merge data provided by a vehicle control unit of or in the vehicle and/or by an additional device such as a smartphone, which is in data communication with the vehicle control unit via a radio interface, together with data provided by the multi-function watch. A coupling of the multi-function watch to a vehicle control unit makes it possible advantageously to transmit data provided by the vehicle control unit such as the vehicle speed, the vehicle interior temperature, external temperature and other weather data to the multi-function watch and output it, in particular to display it there. In this case, data can also be provided or transmitted that a vehicle control unit has in turn downloaded from an external source, such as a weather service via a vehicle-based internet connection and/or by means of a so-called car2X link from another vehicle, or a vehicle-external infrastructure. Such data can contain, for example, information on the traffic situation affecting the vehicle, in particular on traffic congestion and/or hazards such as an accident, etc. Known methods and systems of transport telematics for capturing, estimating, prediction and/or control of the traffic situation can be used here.

The data transmitted to the multi-functional watch can be further processed in the multi-function watch as required and, in particular, for controlling at least one function of the multi-function watch. Conversely, data provided by the multi-function watch and in particular data collected by sensors, such as the body temperature of the vehicle driver, can be transferred by means of the radio interface to a vehicle control unit and output via this, in particular displayed, in the vehicle. The transmitted data can also be further processed in a vehicle control unit as desired and used for controlling other vehicle functions. In extreme cases, e.g. in the event of a sharp drop in the heart rate, an emergency response is initiated in the vehicle such as a fully or partially automatic redirection towards the next available car park and/or the automatic placement of an emergency call to a rescue control center via a mobile wireless interface of the vehicle. On the basis of the transmitted data, functions of other control units and/or devices can also be controlled and in these in particular, functions provided in the vehicle can be disabled, for example an entertainment system of the vehicle permanently integrated into the vehicle (radio, DVD, MP3-player and/or TV) and/or a device temporarily connected to the vehicle for data communication purposes, for example via a radio interface, such as a smartphone, a tablet PC and/or separate entertainment system.

In accordance with the particular aspect of the invention, a system can also be specified for controlling the function of an electronic multi-function watch which is wearable on the arm by a vehicle driver while traveling in a vehicle, the multi-function watch having at least one sensor and one radio interface. The system comprises at least one sensor, which is set up for collecting physiological data of the vehicle driver and/or data from the journey. It also comprises a control unit, which is set up for generating an idle signal in accordance with the collected data, by which a control unit of the multi-function watch shuts off at least one predefined function of the multi-function watch. The system, also known as a control system, can in particular form a component of the multi-function watch. The sensor of the control system can be in particular the sensor of the multi-function watch. The control unit of the control system can be in particular the control unit of the multi-function watch.

The control system can in particular comprise the multi-function watch with at least one of the following components:
 a microprocessor,
 a radio interface,
 a volatile electronic memory,
 a non-volatile electronic memory,
 a display unit,
 a tactile interface and
 a loudspeaker.

In particular, by the targeted control of the function of a tactile interface, for example by suppressing the output of tactile signals or shutting down the entire interface, a distraction for the vehicle driver can be avoided, because vibration is often used in multi-function watches for signaling messages on the watch and can be distracting.

In the context of the particular aspect of the invention, a computer program product can also be specified for controlling the function of an electronic multi-function watch worn on the arm by a vehicle driver while traveling in a vehicle, the multi-function watch having at least one sensor and one radio interface. The computer program product when loaded and executed on at least one computer effects the following steps:
 collecting physiological data of the vehicle driver and/or data from the journey and
 in accordance with the data collected, switching off at least one predefined function of the multi-function watch by a control unit of the multi-function watch.

The computer program can be loaded and executed on two computers using two interacting program modules, e.g. one module on a controller of the vehicle, e.g. for recording driving data and for generating an idle signal when the driving data indicate that the current driving situation requires a very high level of attention of the vehicle driver. The second module can be loaded and executed on the multi-function watch, e.g. for shutting down the SW display after receiving the idle signal.

In particular, the idle signal can be generated in a controller of the vehicle and then sent to the multi-function watch by means of a radio interface. The idle signal can also be generated in the multi-function watch. Via the radio interface a bidirectional communication can advantageously take place between the controller of the vehicle and the multi-function watch.

In accordance with an advantageous embodiment of the invention, the at least one predefined function to be disabled comprises
 the output of graphical information via a display unit of the multi-function watch,
 the output of acoustic information via a loudspeaker of the multi-function watch,
 the output of tactile information via a tactile interface of the multi-function watch,
 the collection of data by at least one predefined sensor,
 the output of data by at least one predefined data interface,
 the processing of predefined data and/or
 the execution of at least one predefined application program.

In accordance with a further advantageous embodiment of the invention, the idle signal is formed before it is sent to the radio interface. The idle signal can be formed using predefined rules, in particular by using the following input variables:

physiological data of the vehicle driver, such as his pulse rate, body temperature, blood pressure, sweat secretion, pupil movement and/or facial expression, and/or load-typical data, such as the physiological data and/or data derived from it and/or data on the traffic situation, the driving situation and/or weather conditions.

In particular for the load-typical data, a preprocessing of data provided by vehicle sensors and/or by car2X-communication can be carried out in a vehicle controller. This can also include an evaluation of the traffic situation and/or driving situation and if necessary, a corresponding characteristic value can be output.

With the particular aspect of the invention, a multi-function watch and/or a controller for a multi-function watch may in particular be provided in such a way that the multi-function watch can assume an operating state in which at least one function in it is automatically deactivated when data supplied by the multi-function watch and/or by a device connected thereto for data communication purposes correspond to at least one predefined rule. The rule can in particular correspond to a situation in which the particular wearer of the multi-function watch finds himself in an overloaded or health-impaired status, e.g. in a state of stress, and/or in a critical traffic situation.

In a further advantageous embodiment of the invention, the deactivation of the at least one function of the multi-function watch is logged by corresponding data being stored in an electronic data medium. Relevant usage data can also be logged, such as date and time of the deactivation. The log can be provided with a suitable signature by a device or a controller.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
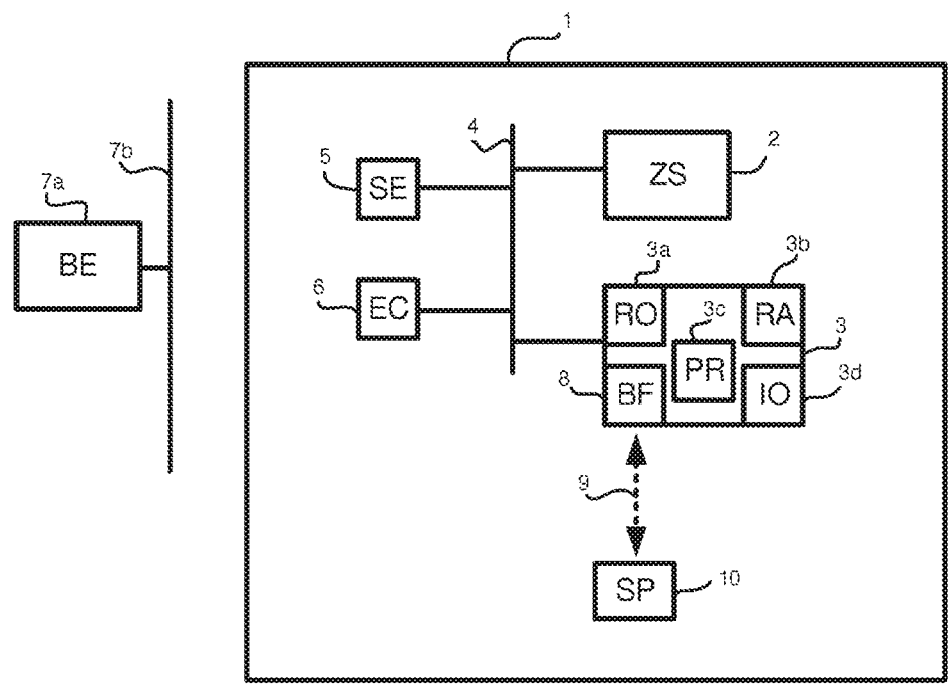
FIG. 1 schematically illustrates a motor vehicle in which a smartphone is used in accordance with an embodiment of the present invention.

In the motor vehicle 1 shown in FIG. 1 a central electronic controller (ZS) 2 is provided, which is connected to other electronic components 3, 5, 6 etc. of the motor vehicle 1 via a typical data bus system 4 of a vehicle comprising, for example, a CAN-Bus, a Flexray-Bus, a MOST-bus and/or an Ethernet bus. As an example, shown here are a sensor system (SE) 5 which comprises a vehicle camera, with which the current traffic density in the environment of the motor vehicle 1 can be detected, and an electronic controller (Electronic Control Unit ECU, EC) 6, which acquires and controls dynamic driving variables, for example in the form of an engine control unit.

The motor vehicle 1 also contains a central information input and/or output device (Head Unit, HU) 3 connected to the bus system 4. It also serves as a human-machine interface (HMI). The head unit 3 comprises at least one input/output unit 3d for this purpose, wherein for the output in particular a graphical output device is provided in the form of a first display screen. It can also comprise another, in particular a further output device, such as a speaker system and/or a so-called head-up display, with which information to be output can be made to appear directly in the field of view of the motor vehicle driver, in particular projected onto the windshield. The display screen can be designed as a so-called touch-screen display, with which the manual input of information is also possible. A different input means can also be provided, for example, a keyboard, a touch panel (touch-pad) and/or a rotary/pushbutton actuator such as the iDrive Controller known in BMW vehicles.

The head unit 3 further comprises a radio interface (BF) 8, via which data can be sent and received wirelessly by radio and which can be designed, for example, according to the Bluetooth standard and/or a different wireless standard, such as e.g. WLAN, NFC and/or GSM G2/G3/G4/G5 etc. In the example shown, via a radio connection 9 a data exchange is possible with a multi-function mobile wireless device (smartphone, SP) 10, which is carried in the motor vehicle 1 during the journey. The radio connection 9 is designed according to at least one common standard for smartphones, such as Bluetooth, NFC and/or WLAN. Via the radio interface 9, the head unit 3 can transmit control signals to the smartphone 10 and preferably also receive control signals.

In particular, via the radio interface 8 the head unit 3 of the motor vehicle 1 can also communicate with electronic control units of other vehicles, for example via a so-called Car2Car communication link. Using the radio interface 8, via a mobile radio link a connection to the internet 7b and/or to a central backend computer (BE) 7a can also be set up, for example, which can exchange data with a plurality of vehicles and supply infrastructure data such as weather forecasting data, traffic flow data in the environment or on a current driving route of the motor vehicle 1, etc.

The head unit 3 also comprises multimedia facilities such as an MP3 player, a radio receiver, etc. Application programs can also be installed in the head unit 3, for example using the radio interface 8 or by any other data connection, e.g. via the databus system 4, where they can be run, displayed and/or operated. An application program with a predefined function can then in particular run on another device, such as the smartphone 10, and can be operated via the output/input unit 3d of the head unit 3. This enables in particular graphic objects of the respective application program to be displayed on the head unit 3 and operator inputs to be made via the head unit 3.

Using the sensor 5, the control device 6 and/or the head unit 3, data relating to the journey are collected, such as the speed, distance traveled, driving time since the start of the journey and/or the prevailing weather conditions, in particular precipitation, visibility conditions (fog), time of day etc. From such data a first, travel-related characteristic value is then formed which is representative of how tiring the journey has been for the vehicle driver so far and/or is currently, i.e. how loaded and/or stressed the driver is from the journey.

To control the processes that are running in the head unit 3 for collecting the data, forming the characteristic value and/or forming the driving situation value, a micro-processor (PR) 3c is provided in the head unit 3, on which a computer program temporarily stored in a Random Access Memory (RAM, RA) 3b is running. The computer program is also permanently stored on the non-volatile memory (read-only memory, ROM, RO) 31 of the head unit. In the memory 3a and/or 3b, additional data, such as control data on control parameters, reference data, data collected in the course of the process, data formed in the course of the process and/or data of a characteristic value are permanently or temporarily stored.

In one process step, reference data relating to the respective vehicle driver are collected, for example from a database stored in the head unit 3 or retrieved from a database of a vehicle-external server which is accessible via an internet connection. The reference data are representative of the degree to which the driver of the vehicle can be loaded, both in general and/or in particular driving situations. For example, for a first vehicle driver who wears a visual aid, a journey in the rain and/or at night can be deemed to be more stressful than for a second driver without a visual aid.

In addition, using suitable sensors in the motor vehicle 1 data can currently be collected on the current mental, physical and/or emotional state of the vehicle driver, for example by means of an interior camera directed at the vehicle driver's face and the data from which are suitably evaluated using image processing software. For example, this can be used to detect an eye blinking rate at a higher frequency than a limit value and thereby infer that the driver of the vehicle is tired. Accordingly, a situation-specific dataset for the vehicle driver is formed, which is characteristic of fatigue. For determining the degree of attention of the vehicle driver a test for the motor vehicle driver can also be carried out using the input and/or output interface 7 of the head unit 3. Then, for example as a test task, characters and images can be output on a display of the input and/or output interface 7, which must be assigned to one another. On the basis of the time that the driver of the vehicle requires for solving the test task and the number of errors, a value for the degree of fatigue can be determined. In particular, reference values from the same vehicle driver from previous, corresponding tests may also be used.

From the individual reference data specific to the vehicle driver and/or the situation-specific data set, a person-specific characteristic value is formed for the vehicle driver, which is representative of the current personal performance of the vehicle driver.

From the travel-related characteristic value and the person-specific characteristic value, an overall characteristic value is formed that is representative of the loading situation of the vehicle driver in his current driving situation.

Using the overall characteristic value in the head unit 3 a driving situation signal is formed which is transmitted to the smartphone 10 via the radio interface 8 and the wireless link 9 and which is representative of the loading situation of the vehicle driver in his current driving situation. The driving situation signal can in particular be exactly the same as the characteristic value or be derived from it, or carry less information or more information than the characteristic value.

The driving situation signal can also contain at least one information item on applications or functions, which either can and/or cannot be used in a controller of the motor vehicle 1, in particular in the head unit 3, while driving. For example, the information can include the fact that entertainment functions such as the playback of audio and/or video data should be provided in the motor vehicle 1, and/or that apps are available for use in the motor vehicle 1 and if so, what kind of apps, and/or that certain apps stored on the smartphone 10 can be displayed and/or operated in the motor vehicle.

Data on the formation of the respective characteristic values or the driving situation signal can be received by the head unit 3, for example, from a vehicle-internal control unit such as the engine control unit 6, from a vehicle-internal sensor such as the sensor 5, from any other control unit, a different sensor, in particular provided in the smartphone 10 and/or any other data source, such as a backend computer 7a.

The respective characteristic values are formed in particular in the head unit 3, but they can also be formed either completely or partially in another control device within the vehicle and/or outside of the vehicle. The characteristic values are formed in using predefined rules and in particular supported by software, wherein for example the following input variables can be used:

physiological data of the vehicle driver, such as pulse rate, body temperature sweat secretion and/or blood pressure, and/or load-typical data, in particular the journey-specific data such as speed, etc.

If the smartphone 10 receives the driving situation signal, it uses it to control at least one predefined function of the smartphone using its microprocessor 13 and the computer program running thereon. The control is effected in such a way that a degree of stress of the vehicle driver when using the function is adapted to suit the degree of stress on the vehicle driver corresponding to the current control of the vehicle. This is achieved in particular by a comparison of a corresponding stored value for the respective function or application, which characterizes the degree of stress on the vehicle driver when using the function, with the characteristic value corresponding to the driving situation signal that characterizes the level of stress on the vehicle driver corresponding to the current control of the vehicle. If the current degree of stress on the vehicle driver caused by controlling the vehicle is above a specified limit, which is obtained from the degree of stress when using the function, then a signal is output to indicate that the function is not enabled and in particular should be deactivated. The limit value can be obtained, for example from the arithmetic calculation $GW=1-GB$, where GB is the degree of stress when using the function, measured in a % value. The 100% value indicates a level at which the driver of the vehicle is fully loaded and has no more corresponding reserves to complete appropriate additional tasks. For the evaluation of the respective working load, a level of working load can be formed for a mental or cognitive working load, for an emotional working load and/or for a physical working load. If a combined value is formed from several such load levels as a sum, then the respective individual working load levels can be associated with suitable, for example, empirically determined weighting factors. This enables in particular the number and/or the particular nature or complexity of the applications or functions of the smartphone 10 available to the vehicle driver to be controlled according to his current loading capacity.

With the invention it is possible in particular that, during a partially or fully autonomous or highly automated journey (HAF) and a very low working load level of the vehicle driver associated therewith, in particular for a driving-related working load level of zero, applications and/or functions on one or more electronic multi-function devices are allowed to be operated to their full extent when driving. In particular, all applications and/or functions on the respective multi-function device available to a user are fully enabled for operation and/or for use.

In order to control a plurality of functions or applications in the smartphone 10, it may in particular be provided that priority values are assigned to the respective applications. On the basis of the priority values and in the present case the at least one characteristic value for the driving situation and/or for the driver stress, it is possible to then successively examine the respective functions/applications in the order of priorities as to how each of them should be controlled for the given characteristic value, i.e. whether a function/application can be enabled and if so, with which control parameters. Applications/functions can also be grouped together and prioritized and the examination can also be carried out in groups. For the individually activated functions/applications and, if appropriate, their respective control parameters, a total can then be formed, i.e. a so-called attentiveness total, which represents the attention of the vehicle driver necessitated by all enabled functions/applications. If during the successive examination of the functions/applications, for any priority value assigned to a function/application (or a group of such), the attentiveness total reaches or exceeds a value which corresponds to the attentiveness available to the driver of the vehicle in the current driving situation, then this may cause functions/applications to which this priority value and/or a lower priority value is assigned to be controlled in a predefined way. In this case, in particular they cannot be activated or deactivated. They can also be controlled using a control parameter in such a way that the use of the function/application is enabled with a minimum necessary level of user attention, in particular without user attention, for example by being run in the background and in particular without the possibility of user interaction.

Each function to be controlled can be coded in the driving situation signal, or in a corresponding dataset. To define the respective function to be controlled, predefined rules can be stored in the head unit 3, in particular in a selectable manner. For example, it can be defined that in a first operating state, in which the vehicle driver has a normal or slightly increased pulse rate between 80 and 100 beats per minute, all the functions and applications may be used with the exception of game applications on the smartphone. If the pulse rate is higher than 120, then only applications with a relatively high priority value, so-called basic applications, can be enabled in the smartphone 10, for example, applications for the mobile wireless functions (voice and data), but for example no applications related to social networks, email editing, etc., which have a relatively low priority value.

The definition of which function or application is controlled and in particular switched off in each case, for example the definition of the priority values, may also be performed within the smartphone 10. It can be set, for example, on the basis of parameter values, which can be selected in particular by the respective user of the smartphone 10 and/or by the vehicle driver. The definition of the respective attentiveness values can be performed in particular by the motor vehicle manufacturer 1, by the manufacturer of the respective smartphone 10 and/or the manufacturer of the respective application program and corresponding control values saved in the respective system (control unit/computer program).

Via the radio interface 8 of the head unit 3 it is also possible for at least one other device, such as a second smartphone, not shown in FIG. 1, a tablet PC, an audio/video playback device, etc. to be connected to a controller of the motor vehicle 1, in particular to the head unit 3 by control technology.

On the basis of the characteristic value or driving situation signal, at least one function of the other device can also be switched off.

Using the driving situation signal, a further function can also be controlled either in the smartphone 10, in a control device of the motor vehicle 1 and/or in the additional device, such as the output of a warning, and in particular activated. For example, in the example given above in the case of a pulse rate of 160 or more, an audible warning can be issued to the driver via a loudspeaker in the head unit 3 and an instruction can be issued that he immediately stop driving and take a rest.

In the head unit 3, the smartphone 10 and/or another device, the relevant characteristic values and/or the driving situation signal can be logged, possibly also including which function was then controlled and how, or which values were accordingly set in the smartphone 10, in the relevant application program and/or the respective other device. The data can be logged, for example, by storing them in a digital, non-volatile memory, wherein a time stamp related to the stored data is also preferably generated and saved. In addition, a signature can be generated by a respectively suitably configured unit and stored with the logged data.

Figure 2:
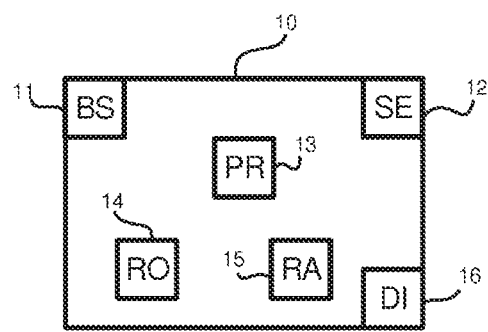
FIG. 2 schematically illustrates the smartphone as in FIG. 1

FIG. 2 shows a smartphone 10 with some selected electronic components, namely a radio interface (BS) 11, which conforms to the wireless standard (Bluetooth, NFC or WLAN) of the vehicle-side radio interface 8 for setting up the radio connection 9 (FIG. 1). It also comprises at least one sensor (SE) 12 for measuring physiological or medical parameters of the vehicle driver. Also, a suitable sensor for measuring the body temperature, blood pressure and/or an appropriate moisture sensor for measuring the sweat emitted by the vehicle driver can be provided, for example. A sensor for journey-specific data, such as a GPS sensor which detects the geographical position, an acceleration sensor and/or a speed sensor can also be provided in the smartphone 10.

The smartphone 10 also has a microprocessor 13, in which a computer program stored in the volatile electronic working memory (Random Access Memory, RAM, RA) 15 of the smartphone 10 is running. The computer program 13 is additionally saved in a non-volatile memory (read-only memory, ROM, RO) 14 in order to make it available even after the smartphone 10 is shut down. The computer program, which can be optionally loaded into the smartphone 10 in particular in the form of an app, is used to control the possible deactivation of a respective function after receipt, or the formation of the driving situation signal.

To provide the graphical output of information, the smartphone 10 has an electronically controllable display 16. The display 16 can be switched off by a driving situation signal generated in the smartphone 10 or received thereby if the latter displays, for example, a very high current loading of the vehicle driver.

The driving situation signal can be formed in a vehicle-internal controller such as the head unit 3. It can also be formed within the smartphone 10. It can also be formed in a control unit outside of the motor vehicle 1, for example in the backend computer 7a (FIG. 1). A particular control unit which contributes to the formation of the driving situation signal can be connected in particular to a medical database, in which general medical data and/or medical or physiological data specific to the vehicle driver are stored, such as a typical resting pulse value of the vehicle driver. Depending on such medical data, parameters and/or rules for forming the driving situation signal can be set or selected.

Figure 3:
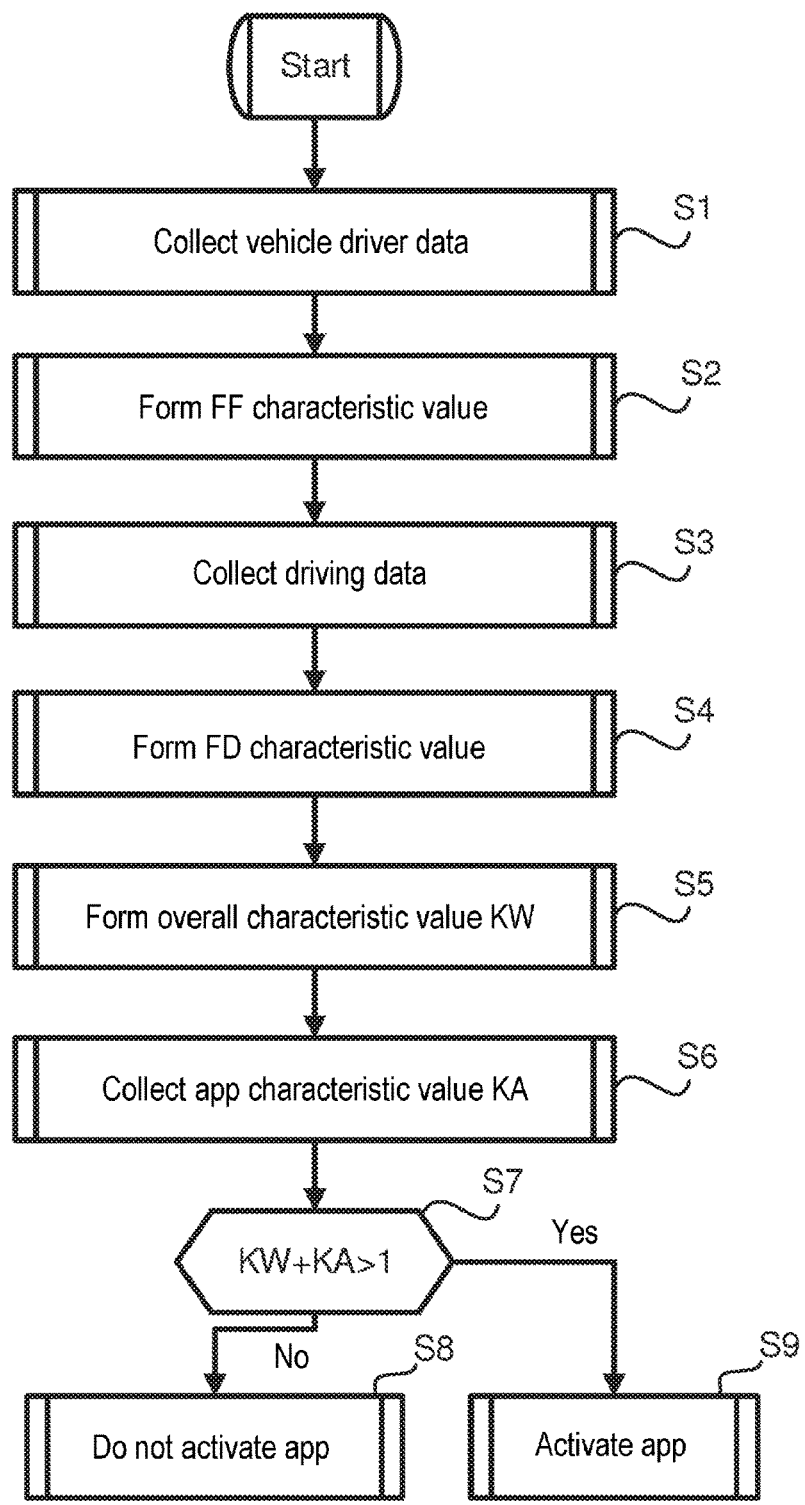
FIG. 3 shows a flow diagram usable with the vehicle of FIG. 1.

FIG. 3 shows a flow chart for controlling a multi-function mobile wireless device, which is operated by a vehicle driver in a vehicle while driving. In step S1 data of the vehicle driver are recorded, from which his current stress level while controlling the vehicle can be determined. The data can correspond to cognitive, physical and/or emotional parameters. For example, they can comprise the pulse rate and/or frequency of eye blinks. In step S2, from the data recorded in step S1 a personal characteristic value FF is formed by means of which the current stress level of the vehicle driver in controlling the vehicle can also be determined. According to the personal characteristic value FF, in particular a driving situation signal can be output.

In step S3 driving data are recorded, from which the current stress level due to the control of the vehicle can be determined. The driving data can comprise, for example, dynamic driving data of the vehicle such as the current vehicle speed, longitudinal and/or lateral acceleration. They can also comprise the traffic density and/or weather data. In step S4, from the data recorded in step S3 a journey-specific characteristic value FD is formed, from which the current stress level of the vehicle driver in controlling the vehicle can also be determined. According to the journey-specific characteristic value FD, in particular a driving situation signal may be output.

In step S5, from the person-specific and journey-specific characteristic values FF and FD an overall characteristic value KW is formed, which is characteristic of the stress level on the vehicle driver due to his current control of the vehicle. The characteristic value can be output in %, in which case it then indicates the degree to which the vehicle driver is stressed relative to a maximum performance level. As the value of the maximum performance it is possible to use a reference value which was determined, e.g. statistically, for an average person. A specific value determined for the individual vehicle driver can also be used. According to the overall characteristic value KW, in particular a driving situation signal may be output.

In step S6, data relating to at least one application program (app) and/or to at least one function of the multi-function mobile radio device are collected. The data are in particular representative of the degree to which a user of the respective application program and/or the respective function is stressed due to its use. From the data collected a characteristic value KA is formed, which is representative of the degree to which a user is stressed relative to his maximum performance for all previously recorded application programs and functions. The characteristic value can therefore be specified in %. As the baseline value for the user it is possible to use a reference value which was determined, e.g. statistically, for an average person. A specific baseline value determined for the individual vehicle driver can also be used.

In step S7, it is checked whether the driver of the vehicle has been overloaded due to his current driving task and the simultaneous use of the application/s and/or function/s. This can be performed by testing whether KW+KA>1, if KW and KA are specified in % as described above. As appropriate, in step S8 the application/s or function/s is/are not enabled. Otherwise the application/s or function/s is/are enabled in step S9. Depending on the activation or deactivation in accordance with the steps S8 and S9, in particular a driving situation signal can be output.

The respective driving situation signal can in particular be signed and thus protected against manipulation. It can also be logged.

As a result of the measures described in this document, in particular by blocking or deactivating at least one device function, it is possible in particular to avoid dangerous situations in road traffic due to device usage overloading the vehicle driver while driving. Also, it can advantageously be determined whether the smartphone was used during the journey, if for example, it is recorded or logged in the motor vehicle, in the smartphone or in another device, such as the backend computer. Other data can also be logged at the same time, for example which function/application has been disabled and/or which output data (sensor values, etc.) were present that gave rise to the driving situation signal.

Although on the basis of the figures the example of a mobile, electronic multi-function device in the form of a smartphone has been described, the method steps, systems and components described there can also be used in conjunction with one or more other mobile electronic multi-function devices, in particular carried in a vehicle. In that regard, the term smartphone used above can usually be replaced by the term electronic multi-function device. Examples of other multi-function devices are those with an audio and/or video device, such as an MP3 player, a DVD playback device, a video camera, a television, a games console, a computer, in particular with a laptop or a tablet PC and respective applications and/or functions available on such devices, including access to a communication network.

The devices and system components described are controlled in particular using computer programs. The invention can therefore also be implemented wholly or partially in the form of a computer program product, which when loaded and executed on a computer either wholly or partially effects a process according to the invention. For example, it may be provided in the form of a data medium such as a CD/DVD, or else in the form of one or more files on a server, from which the computer program can be downloaded.

It has often been stated above that the processes which are run for collecting the data, forming the characteristic value and/or forming the driving situation are controlled by the head unit 3 of the vehicle and that the particular application or function controlled is executed in the portable smartphone 10, which is detachable from the vehicle and/or independently operable. In the context of the invention however, it can also be provided that the respective function is executed in an electronic multi-function device permanently fitted in the vehicle, such as the head unit 3, and is controlled by a control device permanently fitted to the vehicle, such as the central controller 2, the electronic control unit (ECU) 6 or by the head unit 3 itself. The corresponding control of a function of a multi-function device permanently fitted in the vehicle can also be carried out by a control device that is not permanently fitted in the vehicle, such as the smartphone 10 or the backend computer 7a. To this end, a microprocessor and a working memory and possibly other means can also be provided in each control device, and used in order to enable a computer program to run.

A computer program running on a corresponding control device, in particular a head unit, of a motor vehicle or a backend computer cooperates in particular with a computer program running on the electronic multi-function device, in particular on the smartphone, wherein a first group of sub-steps of an overall process according to the invention can be effected as described above using the computer program running in the respective control device, in particular a motor vehicle control device, and a second group of sub-steps can be effected by the computer program running in the respective electronic multi-function device. The computer program running in the electronic multi-function device can be advantageously supplied, for example, by a motor vehicle manufacturer as an app for download and installation on the relevant electronic multi-function device. The installed app can then be linked by a suitable coupling procedure to the respective control device, in particular to a motor vehicle control device such as the head unit or another vehicle ECU, to facilitate their interaction.

Figure 4:
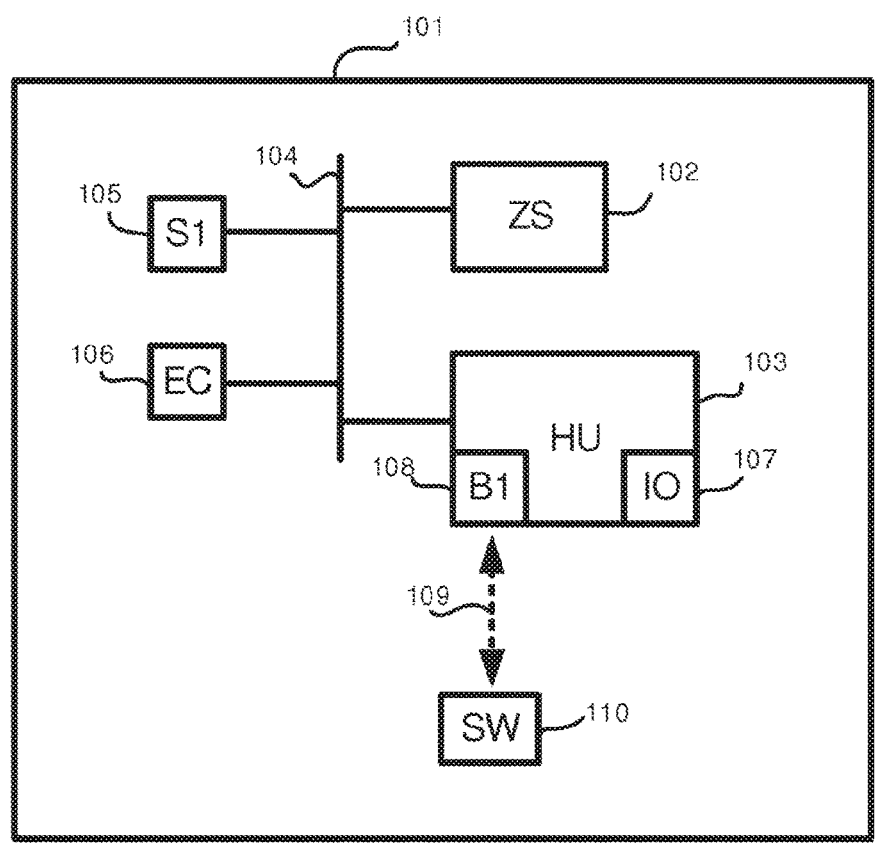
FIG. 4 schematically illustrates an embodiment of the present invention in a motor vehicle with a multi-function watch.

In the motor vehicle 101 shown in FIG. 4 a central electronic controller (ZS) 102 is provided, which is connected to other electronic components 103, 105, 106 etc. of the motor vehicle 101 via a typical vehicle databus system 104 comprising, for example, a CAN-Bus, a Flexray-Bus, a MOST-bus and/or an Ethernet bus. As an example, shown here are a first sensor system (S1) 105 which comprises a vehicle camera, with which the current traffic density in the environment of the motor vehicle 101 can be detected, and an electronic controller (Electronic Control Unit, ECU, EC) 106, which acquires and controls dynamic driving variables, for example in the form of an engine control unit.

The motor vehicle 101 also contains a central information input and/or output device, known as a head unit (HU) 103, connected to the bus system 104. It is also used as and in particular comprises a human-machine interface (Human Machine Interface, HMI) for the input/output of data (IO, 107). The Head Unit 103 comprises at least one input/output unit for the purpose, wherein for the output in particular a graphical output device is provided in the form of a first display screen. It can also comprise another, in particular a further output device, such as a speaker system and/or a so-called head-up display, with which information to be output can be made to appear directly in the field of view of the motor vehicle driver, in particular projected onto the windshield. The display screen can be designed as a so-called touch-screen display, with which the manual input of information is also possible. A different input means can also be provided, for example, a keyboard, a touch panel (touchpad) and/or a so-called scroll wheel such as the iDrive Controller familiar from BMW vehicles.

The head unit 103 further comprises a radio interface (B1) 108, via which data can be sent and received wirelessly by radio and which can be designed, for example, according to the Bluetooth standard and/or a different wireless standard, such as e.g. WLAN, NFC or GSM G2/G3/G4/G5 etc. In the example shown, a data exchange with a multi-function watch (Smart Watch, SW) 110 is possible via a radio connection 109, which is worn by the driver of the motor vehicle 101 on his arm and is thus located in the motor vehicle 101 while driving. The radio link 108 is designed in accordance with at least one common standard for smartphones or smart watches, such as Bluetooth, NFC and/or WLAN. Via the radio interface 108, the head unit 103 can transmit control signals to the multi-function watch 110 and preferably also receive control signals. Alternatively, the Smart Watch 110 can be indirectly coupled to the vehicle 101 or to its head unit 103 via a multi-function mobile wireless device (smartphone), wherein the Smart Watch 110 and the head unit 103 in each case only communicate directly with the smartphone, or in particular are only in radio contact with it. The smartphone then acts in particular as a relay station.

In particular, via the radio interface 108 the head unit 103 of the motor vehicle 101 can also communicate with electronic control units of other vehicles, for example via a so-called Car2Car communication link. Using the radio interface 108, for example, a connection to the internet and/or to a central, so-called backend computer can also be set up via a mobile radio connection, which can exchange data with a plurality of vehicles and can supply infrastructure data, such as weather forecast data, traffic flow data in the locality or on a current driving route of the motor vehicle 101, etc.

If on the basis of data which it receives and/or data generated in it an increased loading on the vehicle driver compared to a normal operation of the motor vehicle 101 and/or a health-related limitation of the vehicle driver can be inferred, the head unit 103 generates an idle signal and sends it to the multi-function watch 110 over the radio interface 109 or the radio link 109. The head unit 103 can receive the respective data for forming the idle signal, for example, from a vehicle-internal control unit such as the engine control unit 106, from a vehicle-internal sensor such as the sensor 105, from another control unit, another sensor, in particular provided in the multi-function watch 110 and/or any other data source, such as a backend server.

The idle signal is formed in particular in the head unit 103 using predefined rules, in particular the following input variables being used:
  physiological data of the vehicle driver, such as pulse rate, body temperature, sweat secretion and/or blood pressure, and/or
  load-typical data.

When the multi-function watch 110 receives the idle signal it switches off the predefined functions. The respective function to be switched off can be coded in the idle signal, or in an appropriate idle mode dataset. To define the particular function to be switched off, predefined rules can be stored in the head unit 103, in particular in a selectable manner. For example, it can be defined that in a first operating state, in which the vehicle driver has a slightly increased pulse rate between 80 and 100 beats per minute, only the time of day and the heart rate are displayed in the display of the multi-function watch 110. If on the other hand the pulse rate is higher than 120, then the display of the multi-function watch is switched off completely.

The definition of which function is switched off in each case can also be made within the multi-function watch 110, for example on the basis of parameter values which can be set in particular by the respective user of the multi-function watch. They can also be defined within the multi-function watch 110 on the basis of sensor values and predefined rules, which are recorded e.g. with the multi-function watch 110 and/or applied.

Via the radio interface 108 at least one other device such as a smartphone can also be connected to a controller of the motor vehicle 101, in particular to the head unit 103, using control technology. On the basis of the idle signal sent to the multi-function watch 110, at least one function of the other device can also be switched off.

Using the idle signal, another function can also be activated in the multi-function watch 110, in a control device of the motor vehicle 101 and/or in the additional device, such as the output of a warning. For example, in the example given above in the case of a pulse rate of 160 or more, an audible warning can be issued to the vehicle driver via a loudspeaker in the head unit 103 and an instruction can be issued that he immediately stop driving and take a rest.

Both a function to be deactivated and a function to be activated in the multi-function watch, in the vehicle or in the additional device, can each comprise:
  the output of graphical information via a display unit,
  the output of acoustic information via a loudspeaker,
  the output of tactile information via a tactile interface,
  the collection of data by at least one predefined sensor,
  the output of data by at least one predefined data interface, the processing of predefined data, the execution of at least one predefined application program.

Figure 5:
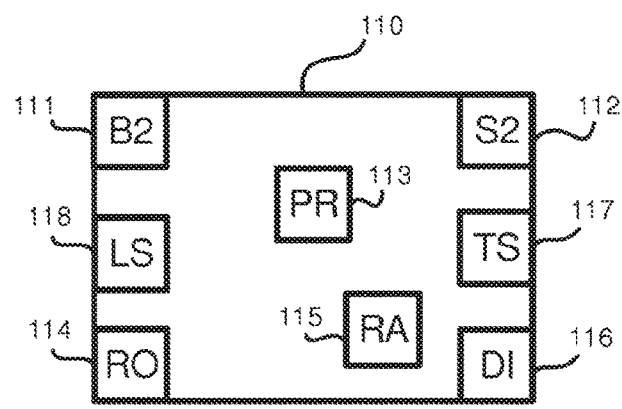
FIG. 5 schematically illustrates electronic components of the FIG. 4 multi-function watch.

FIG. 5 shows a multi-function watch 110 with some selected electronic components, namely the radio interface (B2) 111, which conforms to the wireless standard (Bluetooth, NFC or WLAN) of the vehicle-side radio interface 108 for setting up the radio connection 109 (FIG. 1). It also comprises at least one sensor (S2) 112 for measuring physiological or medical parameters, for example, a pulse sensor, which normally is in contact with the inside of the wrist of the vehicle driver such that the vehicle driver's pulse can be measured.

Also, a suitable sensor for measuring the body temperature, blood pressure and/or an appropriate moisture sensor for measuring the sweat released by the vehicle driver can be provided, for example.

The multi-function watch 110 also has a microprocessor 113, in which a computer program is executed that is stored in the volatile electronic working memory (Random Access Memory, RAM, RA) 115 of the multi-function watch 110. The computer program 113 is also stored in a non-volatile memory (Read-Only Memory, ROM, RO) 114 in order for it to be available even after a possible shutdown of the multi-function watch 110. The computer program, which can be optionally loaded into the multi-function watch 110 in particular in the form of an app, is used to control the possible deactivation of a respective function after receipt or formation of the idle signal.

For the graphical output of information such as the time of day, pulse etc., the multi-function watch 110 comprises an electronically controllable display 116. In particular, the display 116 can be switched off by an idle signal generated in the multi-function watch 110 or received thereby. For outputting tactile information, in particular a tactile feedback for example by vibration, the multi-function watch 110 comprises an electronically controllable tactile interface 117. For outputting acoustic information, e.g. on the time of day or the pulse rate, the multi-function watch 110 comprises a loudspeaker 118.

The idle signal can be formed in a vehicle-internal controller such as the head unit 103. It can also be formed within the multi-function watch 110. It can also be formed in a control unit outside of the motor vehicle 101, for example in a backend computer. A particular control unit which contributes to the formation of the idle signal can be connected in particular to a medical database, in which general medical data and/or personal medical or physiological data specific to the vehicle driver are stored, such as a typical resting pulse value of the vehicle driver. Depending on such medical data, parameters and/or rules for forming the idle signal can be set or selected.

As a result of the measures described in this document, in particular by blocking or deactivating at least one device function, it is possible in particular to avoid dangerous situations in road traffic due to the use of a device while driving. In addition it can be advantageously determined whether the multi-function watch was used during the journey, if for example, it is recorded or logged in the motor vehicle, the multi-function watch or another device such as the backend server, in particular using a time stamp and/or a signature, that an idle signal has been generated, received and/or transmitted. Further data can be logged at the same time, for example which function was deactivated and/or which output data (sensor values, etc.) were present which gave rise to the idle signal.

It can be stated again:

the smart watch or multi-function watch can in particular be an accessory that the driver carries, uses or wants to use while driving, be used for measuring physiological or medical parameters, e.g. for a pulse measurement of the driver, and comprise suitable sensors for the purpose and/or be designed to communicate with the vehicle or with a control system of the vehicle.

The proposed controller or computer program application (app) can in particular estimate the loading of the driver (e.g. via the pulse, the traffic situation/driving situation, communication with a vehicle controller etc.), start or stop the disabling of the respective function of the multi-function watch, and/or log a deactivation or disabling of a function of the multi-function watch and/or appropriate usage data.

The vehicle can in particular be designed to estimate the traffic situation or driving situation and/or to communicate with the multi-function watch directly and/or indirectly for transmitting data.

The deactivation of at least one function of the multi-function watch allows a disabling of the interaction of the driver with the multi-function watch to be achieved, based on various factors. A function can be disabled in particular if at least one of the listed conditions or indicators is present:

the vehicle speed is above a predefined threshold value (e.g., 30 km/h), it is detected that the driver is under high stress, wherein the detection can occur due to a traffic situation, and in particular can be established via Car2Car or Infrastruktur2Car, e.g. via backend communication. It can also occur via observation of the pulse of the driver, for example with the smart watch or a different smart accessory, such as a piece of jewelry which has a corresponding electronic controller and sensor system.

The devices and system components described are in particular controlled with computer programs, and thus can comprise further known elements of computers and digital control devices, such as a microprocessor, volatile and non-volatile memories, interfaces, and so on. The invention can therefore also be wholly or partially implemented in the form of a computer program product, which when loaded and executed on a computer effects a process according to the invention either wholly or partially. For example, it may be provided in the form of a data carrier such as a CD/DVD or else in the form of one or more files on a server, from which the computer program can be downloaded.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for controlling at least one predefined function of an electronic multi-function device usable by a vehicle driver in a vehicle while driving, the electronic multi-function device being connectable to at least one control unit of the vehicle by a communication link, comprising the acts of:

collecting, using at least one of the electronic multi-function device and the at least one vehicle control unit, at least one of data of the vehicle driver and data from a journey, forming at least one characteristic value which is characteristic of a degree of stress of the vehicle driver due to his current vehicle control based on the collected data, and controlling the electronic multi-function device to control the at least one predefined function of the electronic multi-function device based on the at least one characteristic value, wherein
- the control of the at least one predefined function of the electronic multi-function device based on the at least one characteristic value includes setting an operating state of the at least one predefined function such that a degree of stress of the vehicle driver when using the at least one predefined function is matched to the degree of stress of the vehicle driver due to his current vehicle control, and
- the electronic multi-function device is at least one of a multi-function mobile wireless device and a multi-function watch.

2. The method of claim 1, wherein
the data of the journey is obtainable from at least one of at least one sensor, at least one control unit of the vehicle, and an interface of the vehicle configured to exchange data with a vehicle-independent computer.

3. The method of claim 2, wherein
based on the at least one characteristic value, the electronic multi-function device is controlled to deactivate at least one of the at least one predefined functions.

4. The method of claim 3, wherein
at least one of the at least one control unit of the vehicle provides a driving situation signal based on the at least one characteristic value.

5. The method of claim 4, wherein
the driving situation signal includes information about at least one of
- at least one of control and display options of at least one of the at least one control unit of the vehicle, and
- at least one of a driving situation cognitive relevance, emotional relevance and physical relevance.

6. The method of claim 5, wherein
use of at least one of the control and display options is logged.

7. The method of claim 4, wherein
the driving situation signal includes information about applications usable in the vehicle.

8. The method of claim 7, wherein
use of applications associated with the driving situation signal is logged.

9. The method of claim 7, wherein
a usage of the applications is logged.

10. The method of claim 1, wherein
the at least one predefined function in the electronic multi-function device is assigned a minimum characteristic value corresponding to a minimum level of attentiveness,
use of the at least one predefined function is prevented if the characteristic value formed from the collected data of the vehicle driver and/or the journey is outside a predefined range relative to the minimum characteristic value.

11. The method of claim 1, wherein
in the act of collecting at least one of data of the vehicle driver and data from the journey, the data of the vehicle driver is collected, the data of the vehicle driver being collected using at least one of:

a sensor of the vehicle,
a control unit of the vehicle,
a radio link of the vehicle,
a sensor of the electronic multi-function device,
a control unit of the electronic multi-function device,
internet, and
a vehicle-external computer.

12. The method of claim 11, wherein
at least a part of the data of the vehicle driver is based on at least one task performed by the vehicle driver during the journey and driver performance of the at least one task.

13. The method of claim 11, wherein
the data of the vehicle driver is physiological data,
the at least one characteristic value is based at least in part on the vehicle driver physiological data, and
based on the at least one characteristic value, a control unit of the electronic multi-function device deactivates at least one of the at least one predefined functions.

14. The method of claim 13, wherein
the data of the journey is collected,
the electronic multi-function device is a multi-function watch,
the data of the journey includes data of the vehicle; and
the data of the vehicle is sent by the at least one control unit of the vehicle to the multi-function watch via the radio link.

15. The method of claim 14, wherein
an idle signal for deactivating the at least one predetermined function generated by the at least one controller of the vehicle is sent to the multi-function watch via the radio link.

16. The method of claim 15, wherein
the idle signal is formed using predefined rules, using at least one of
- physiological data of the vehicle driver, the physiological data including at least one of pulse rate, body temperature and blood pressure, sweat secretion, pupil movement and facial expression, and
- load-typical data including at least one of data derived from the physiological data of the driver, data on a traffic situation, and weather conditions.

17. The method of claim 13, wherein
the electronic multi-function device is a multi-function watch, and
at least part of the physiological data of the vehicle driver is collected by at least one sensor of the multi-function watch.

18. The method of claim 17, wherein
an idle signal for deactivating the at least one predetermined function generated by the at least one controller of the vehicle is sent to the multi-function watch via the radio link.

19. The method of claim 18, wherein
the idle signal is formed using predefined rules, using at least one of
- physiological data of the vehicle driver, the physiological data including at least one of pulse rate, body temperature and blood pressure sweat secretion, pupil movement and facial expression, and
- load-typical data including at least one of data derived from the physiological data of the driver, data on a traffic situation, and weather conditions.

20. The method of claim 1, wherein
the at least one predefined function includes at least one of output of graphical information via a display unit of the multi-function watch, output of acoustic information via a speaker of the multi-function watch, output of tactile information via a tactile interface of the multi-function watch, collection of data by at least one predefined sensor, output of data by at least one predefined data interface, processing of predefined data, and execution of at least one predefined application program.

21. A system for controlling at least one predefined function of an electronic multi-function device usable by a vehicle driver in a vehicle while driving, comprising:

at least one control unit of the vehicle connectable to the electronic multi-function device via a communication link;

a detection unit configured to collect data on at least one of the vehicle driver and data on a journey, a data-processing unit configured to form at least one characteristic value based on data collected by the detection unit, the at least one characteristic value being characteristic of a level of stress on the vehicle driver due to his current vehicle control, a control element configured to control at least one predefined function of the electronic multi-function device based on the at least one characteristic value, wherein the control of the at least one predefined function of the electronic multi-function device based on the at least one characteristic value includes setting an operating state of the at least one predefined function such that a degree of stress of the vehicle driver when using the at least one predefined function is matched to the degree of stress of the vehicle driver due to his current vehicle control, and the electronic multi-function device is at least one of a multi-function mobile wireless device and a multi-function watch.

22. A system as claimed in claim 21, wherein the electronic multi-function device is an electronic multi-function watch wearable on an arm of the vehicle driver while traveling in the vehicle, the electronic multi-function watch includes at least one sensor configured to collect at least one of physiological data of the vehicle driver and at least a portion of the data from the journey and at least one radio interface configured to communicate the collected data via a radio link, and at least one of the at least one control unit of the vehicle is configured to generate an idle signal for deactivating the at least one predetermined function of the multi-function watch based on the data collected by the detection unit.

23. The system of claim 21, further comprising:

the vehicle.

24. A computer program product fixed in a non-transitory tangible medium configured to control execution of a method for controlling at least one predefined function of an electronic multi-function device usable by a vehicle driver in a vehicle while driving, the electronic multi-function device being connectable to at least one control unit of the vehicle by a communication link, the method comprising the acts of:

collecting, using at least one of the electronic multi-function device and the at least one control unit of the vehicle, at least one of data of the vehicle driver and data from a journey, forming at least one characteristic value which is characteristic of a degree of stress of the vehicle driver due to his current vehicle control based on the collected data, and controlling the electronic multi-function device to control the at least one predefined function of the electronic multi-function device based on the at least one characteristic value, wherein the control of the at least one predefined function of the electronic multi-function device based on the at least one characteristic value includes setting an operating state of the at least one predefined function such that a degree of stress of the vehicle driver when using the at least one predefined function is matched to the degree of stress of the vehicle driver due to his current vehicle control, and the electronic multi-function device is at least one of a multi-function mobile wireless device and a multi-function watch.

25. A computer program product fixed in a non-transitory tangible medium configured to control execution of a method for controlling an electronic multi-function watch worn on an arm of a vehicle driver while traveling in a vehicle, the multi-function watch having at least one sensor and at least one radio interface, the method comprising the acts of:

collecting at least one of physiological data of the vehicle driver and at least a portion of data from a journey, and controlling, using a control unit of the multi-function watch, deactivation of at least one predefined function of the multi-function watch based on the data collected in the act of collecting at least one of the physiological data of the vehicle driver and the at least the portion of the data from the journey.

* * * * *